US00PP36362P2

(12) United States Plant Patent
Noordam

(10) Patent No.: US PP36,362 P2
(45) Date of Patent: Dec. 31, 2024

(54) ***CAMPANULA* PLANT NAMED 'CAMEDU'**

(50) Latin Name: *Campanula medium*
Varietal Denomination: CAMEDU

(71) Applicant: Kwekerij Stadsland, Waardenburg (NL)

(72) Inventor: Jan Noordam, Waardenburg (NL)

(73) Assignee: Kwekerij Stadsland (NL)

( * ) Notice: Subject to any disclaimer, the term of this patent is extended or adjusted under 35 U.S.C. 154(b) by 0 days.

(21) Appl. No.: 18/429,993

(22) Filed: Feb. 1, 2024

(51) Int. Cl.
*A01H 5/02* (2018.01)
*A01H 6/26* (2018.01)

(52) U.S. Cl.
USPC ..... Plt./414

(58) Field of Classification Search
USPC ..... Plt./414
See application file for complete search history.

(56) References Cited

PUBLICATIONS

CPVO—https://online.plantvarieties.eu/publicSearch?denomination=camedu Retrieved from the Internet on Jun. 4, 2024.*
Cpvo.*

* cited by examiner

*Primary Examiner* — Susan McCormick Ewoldt
(74) *Attorney, Agent, or Firm* — Cassandra Bright

(57) ABSTRACT

A new and distinct cultivar of *Campanula* plant named 'CAMEDU' is disclosed, characterized by biennial plants producing sterile flowers. The unique new cultivar produces white, fully double flowers. Flowers have the novel characteristic of not fading after visits by pollinators. The new cultivar is a *Campanula*, typically produced as an outdoor ornamental plant or for cut flower purposes.

2 Drawing Sheets

Figure 1:
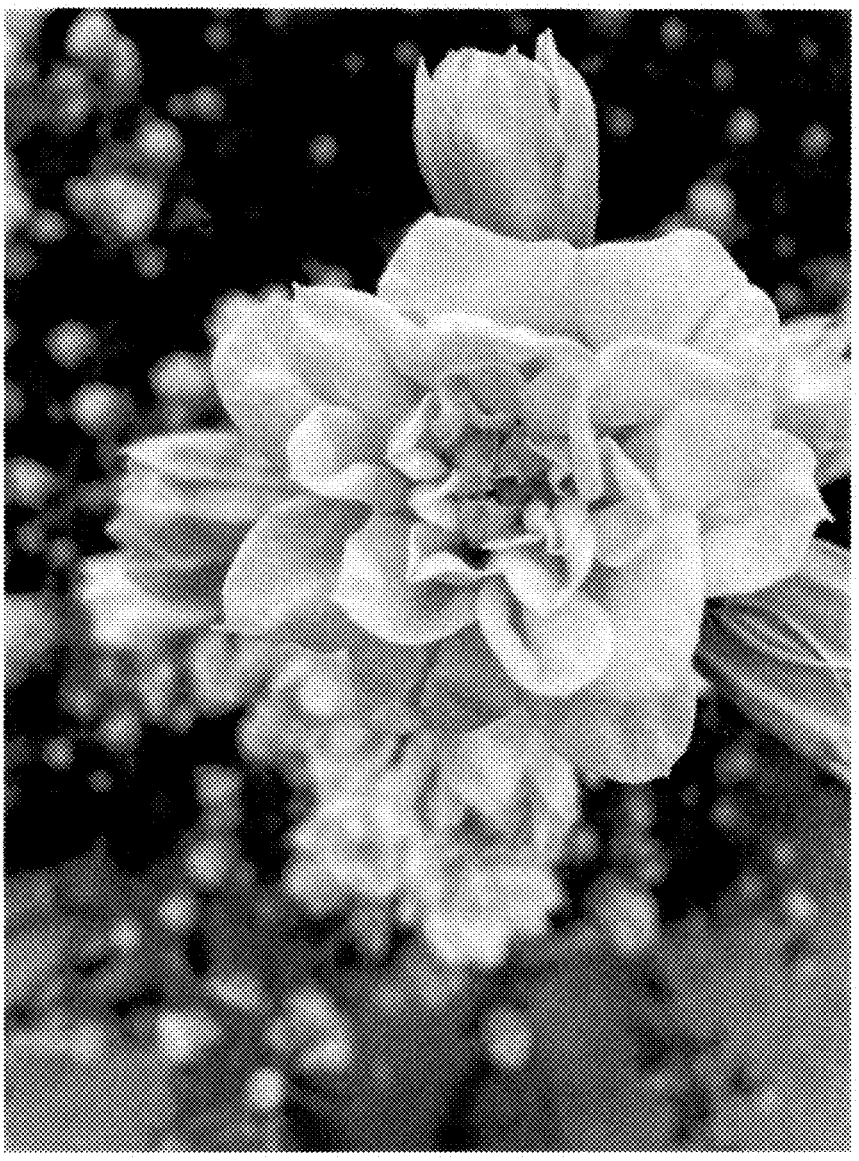

Latin name of the genus and species: *Campanula medium.*
Variety denomination: 'CAMEDU'.

BACKGROUND OF THE INVENTION

The new cultivar is a product of a planned breeder program conducted by the inventor at a commercial nursery in Angeren, the Netherlands. The objective of the breeding program was to produce new *Campanula* varieties for both cut flower and garden use. The cross resulting in this new variety was made during June of 2019.

The seed parent is an unnamed, unpatented variety of *Campanula medium*. The pollen parent is a different unnamed, unpatented *Campanula medium*. The new variety was selected at a commercial nursery in Angeren, the Netherlands in June of 2020.

Asexual reproduction of the new cultivar 'CAMEDU' was first performed during July of 2020 at a commercial nursery in Heerhugowaard, the Netherlands via tissue culture. Through subsequent propagation, multiple additional generations have been reproduced, having shown that the unique features of this cultivar are stable and reproduced true to type.

SUMMARY OF THE INVENTION

The cultivar 'CAMEDU' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CAMEDU'. These characteristics in combination distinguish 'CAMEDU' as a new and distinct *Campanula* cultivar:

1. Sterile flowers.
2. Long lasting flowers with a vase life of 20 to 22 days.
3. Flowers do not fade after visits by pollinators.
4. Biennial plants.
5. White, fully double flowers.

PARENT COMPARISONS

The new variety 'CAMEDU' differs from both the seed and pollen parents in that the flowers of the new variety do not fade as occurs in both parent varieties.

COMMERCIAL COMPARISONS

Plants of the new cultivar *Campanula* 'CAMEDU' can be compared to the commercial variety *Campanula* 'Champion Pink', unpatented. Plants of 'CAMEDU' are similar to plants of 'Champion Pink' in most horticultural characteristics, however, plants of 'CAMEDU' differ in the following:

1. Flowers of the new variety are white; flowers of this comparator are solid pink.
2. Flowers of the new variety do not fade after a visit by a pollinator; flowers of this comparator fade after pollination.
3. Plants of the new variety are biennial; plants of this comparator are typically grown as an annual.

Plants of the new cultivar *Campanula* 'CAMEDU' can be compared to the commercial variety *Campanula* 'Campana Pink', unpatented. Plants of 'CAMEDU' are similar to plants of 'Campana Pink' in most horticultural characteristics, however, plants of 'CAMEDU' differ in the following:

1. Flowers of the new variety are white; flowers of this comparator are solid pink.
2. Flowers of the new variety do not fade after a visit by a pollinator; flowers of this comparator fade after pollination.
3. Plants of the new variety are biennial; plants of this comparator are typically grown as annuals.

BRIEF DESCRIPTION OF THE PHOTOGRAPHS

The accompanying photograph in FIG. 1 illustrates in full color a close up a typical of 'CAMEDU'.

Figure 2:
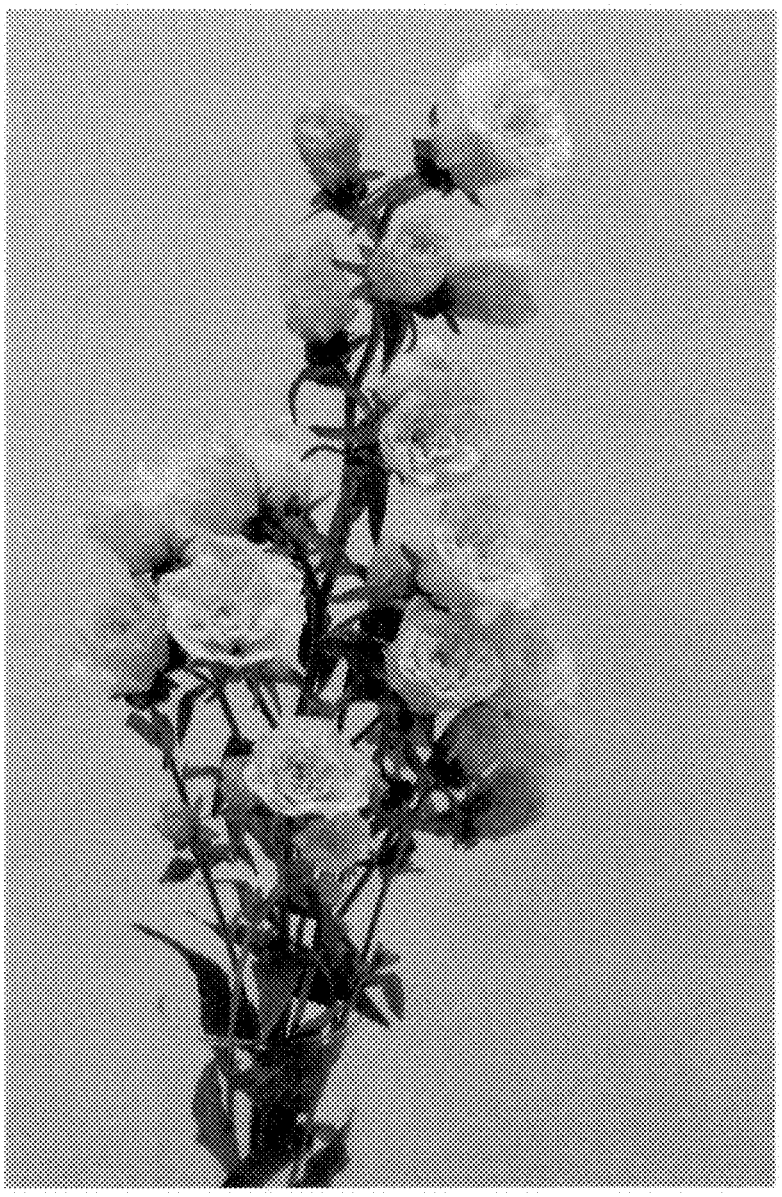

FIG. 2. Illustrates a typical flowering stem from 'CAMEDU' grown in an unheated greenhouse in the Netherlands. This plant is approximately 250 days old, grown in a 1-gallon container.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'CAMEDU' plants grown in the ground in an unheated greenhouse in Angeren, the Netherlands. The plants were about 250 days old. Temperatures ranged from −6° C. to 15° C. at night to 5° C. to 30° C. during the day. No chemical treatments were given to the plants, only biological control for thrips. Measurements and numerical values represent averages of typical plant types.

Botanical classification: *Campanula medium* 'CAMEDU'.

PROPAGATION

Time to initiate roots: About 5 to 10 days at 15° C. to 20° C.

Time to produce a rooted liner: About 35 to 40 days at approximately 20° C.

PLANT

Age of plant described: Approximately 250 days.
Growth habit: Upright.
Height: 70 to 150 cm.
Plant spread: 40 cm.
Growth rate: Moderate.
Main stem characteristics:
- *Length*.—Average 100 cm.
- *Diameter*.—2.0 to 2.5 cm at base.
- *Quantity of stems per plant*.—About 30 to 50 basally emerging stems.
- *Color*.—RHS Green 140D flushed 141 A.
- *Texture*.—Pubescent.
- *Strength*.—Very strong.

Primary lateral branches:
Quantity of primary lateral branches: 6-10.
Length of primary lateral branches: 25-40 cm.
Characteristics of primary lateral branches:
- *Form*.—Round.
- *Diameter*.—0.5-1 cm.
- *Color*.—RHS Green 140D flushed 141 B.
- *Texture*.—Pubescent.
- *Strength*.—Medium.

Internode length: Average range 5-7 cm.
Root description: Dense, fibrous root system. Roots variably white, not accurately measured with R.H.S. chart.

FOLIAGE

Leaf:
- *Arrangement*.—At the base very crowded (rosette). On the stems alternate.
- *Quantity*.—Approximately 150 to 300 per plant.
- *Rosette foliage*.—
- *Average length*.—15 cm.
- *Average width*.—3 cm.
- *Shape of blade*.—Ovate-lanceolate.
- *Apex*.—Acuminate.
- *Base*.—Attenuate.
- *Margin*.—Serrate.
- *Aspect*.—Slightly undulate.
- *Texture of top surface*.—Glabrous.
- *Texture of bottom surface*.—Glabrous.
- *Color*.—Young foliage, upper side: Near RHS Green 141D. Young foliage, under side: Near RHS Green 141D. Mature foliage, upper side: Near RHS Green 141A. Mature foliage, under side: Near RHS Green 141A.
- *Venation*.—Type: Reticulate. Color, upper side: Near RHS Green 140D. Color, under side: Near RHS Green 140D.

Petiole:
- *Length*.—Average 5 mm.
- *Diameter*.—Average 4 mm.
- *Color*.—Near RHS Green 140D flushed 141 B.
- *Texture*.—Pubescent.

FLOWER

Natural flowering season: May and June.
Inflorescence:
- *Type and habit*.—Panicle composed of single campanulate flowers.
- *Height*.—Average range 50 cm to 80 cm.
- *Diameter*.—Average range 20 to 30 cm.
- *Flowers per inflorescence*.—Average range 20 to 30.

Rate of flower opening: 30 to 50 days from bud to fully opened flower.
Flower longevity on plant: 30 to 40 days.
Vase life: 20 to 22 days.
Persistent or self-cleaning: Persistent.
Flower attitude: Upward when young, slightly downward when mature.
Bud:
- *Shape*.—Oval.
- *Length*.—2-3 cm.
- *Diameter*.—1 cm.
- *Color*.—RHS Green 141A.

Flower size:
- *Diameter*.—6.5 to 7 cm.
- *Depth*.—4.5 to 5 cm.
- *Throat diameter*.—2-3 cm.
- *Tube length*.—4-5 cm.
- *Tube diameter at base*.—1 cm.

Petal lobes and tube:
- *Petal lobes*.—Numerous.

*Length*.—3-4 cm.
*Width*.—3-4 cm.
*Shape*.—Broad ovate.
*Apex*.—Rounded.
*Base*.—Fused.
*Texture, outer surfaces*.—Petal Lobe: Soft, glabrous. Tube: Soft, glabrous.
*Texture, inner surfaces*.—Petal Lobe: Soft, glabrous. Tube: Soft, glabrous. Throat: Soft, glabrous.
*Color*.—Outer Surfaces: Petal Lobe when opening: RHS White NN155D. Tube when opening: RHS White NN155D. Petal Lobe fully opened: RHS White NN155D. Tube fully opened: RHS White NN155D. Inner Surfaces: Petal Lobe when opening: RHS White NN155D. Tube when opening: RHS White NN155D. Throat when opening: RHS White NN155D. Petal Lobe fully opened: RHS White NN155D. Tube fully opened: RHS White NN155D. Throat fully opened: RHS White NN155D. Petal Lobe fading: RHS White NN155D. Tube fading: RHS White NN155D. Throat fading: RHS White NN155D.

Sepals:
*Position of the calyx lobes to the corolla*.—Spreading.
*Quantity*.—5.
*Length*.—1.5-2 cm.
*Width*.—1 cm.
*Shape*.—Ovate.
*Apex*.—Acuminate.
*Base*.—Obtuse.
*Margin*.—Serrate.
*Texture*.—Outer Surface: Pubescent, almost bristly. Inner Surface: Smooth.
*Color*.—Outer Surface: Green 141A. Inner Surface: Green 141A.

Peduncles:
*Length*.—1-2 cm.
*Diameter*.—3 mm.
*Angle*.—About 60° to the lateral branch.
*Strength*.—Medium.
*Texture*.—Pubescent.
*Color*.—RHS Green 140D flushed 141B.

Pedicels:
*Length*.—1-2 cm.
*Diameter*.—3 mm.
*Angle*.—About 60° to the lateral branch.
*Strength*.—Medium.
*Texture*.—Pubescent.
*Color*.—RHS Green 141D.

REPRODUCTIVE ORGANS

Stamens:
*Number per flower*.—Typically 5.
*Filament length*.—1 cm.
*Filament color*.—Near RHS White 155C.

Anthers:
*Shape*.—Round.
*Length*.—Approximately 1 cm.
*Color*.—Near RHS White 155C.
*Pollen*.—Scant.
*Pollen color*.—RHS Yellow.

Pistil:
*Quantity per flower*.—1.
*Length*.—Approximately 2 to 3 cm.
*Style*.—Shape: Round. Length: Approximately 2 cm. Color: Near RHS White 155D.
*Stigma*.—Shape: Orbicular.

OTHER CHARACTERISTICS

Seeds and fruits: Sterile; no seed production.
Disease/pest resistance: Neither resistance nor susceptibility to common diseases and pests of *Campanula* has been observed.
Temperature tolerance: Zone 8 hardiness.

What is claimed is:

1. A new and distinct cultivar of *Campanula* plant named 'CAMEDU' as herein illustrated and described.

* * * * *